United States Patent [19]

Tanokura et al.

[11] Patent Number: 5,124,030
[45] Date of Patent: Jun. 23, 1992

[54] SOLUTION SEPARATING APPARATUS

[75] Inventors: Nobukazu Tanokura; Susumu Fujikawa; Susumu Kobayashi; Akihiko Furuya; Fumiaki Inaba, all of Fujinomiya, Japan

[73] Assignee: Terumo Kabushiki Kaisha, Tokyo, Japan

[21] Appl. No.: 573,887

[22] Filed: Aug. 27, 1990

[30] Foreign Application Priority Data

Sep. 5, 1989 [JP] Japan .................................. 1-228221
Sep. 5, 1989 [JP] Japan .................................. 1-228222

[51] Int. Cl.⁵ ...................... B01D 21/26; B01D 21/30
[52] U.S. Cl. ............................................. 210/86; 210/94;
210/109; 210/143; 210/513; 222/23; 222/52;
222/96; 222/103; 222/214
[58] Field of Search ............... 210/86, 94, 97, 513,
210/523, 143, 85, 109; 222/23, 52, 95, 96, 103,
214

[56] References Cited

U.S. PATENT DOCUMENTS 4,350,585  9/1982  Johansson et al. .................. 210/523
4,663,032  5/1987  Loos et al. ........................... 210/97
4,976,851  12/1990 Tanokura et al. ..................... 210/94

FOREIGN PATENT DOCUMENTS 0329786  11/1987  European Pat. Off. .
63-119776  5/1988  Japan .
8501915  7/1985  Netherlands .

OTHER PUBLICATIONS

Patent Abstracts of Japan, vol. 6, No. 38; Interface Detector.

Primary Examiner—W. Gary Jones
Attorney, Agent, or Firm—Frishauf, Holtz, Goodman & Woodward

[57] ABSTRACT

A solution separating apparatus has a container holding portion, a container pressurizing portion, an interface detecting portion, and a control unit. The interface detecting portion comprises a light emitting apparatus disposed to one side and a light receiving apparatus disposed to another side with a container held by the container holding portion sandwiched therebetween. The light emitting element comprises a plurality (three or more) of light emitting elements disposed in parallel in the substantially moving direction of the interface within the container. Another solution separating apparatus embodiment has a container holding portion, a tube clamper, a container pressurizing portion, a control unit, and a weight measuring portion commonly used by two or more container holding portions. The weight measuring portion selectively measures the quantity of weight change of each container held by the container holding portions.

14 Claims, 11 Drawing Sheets

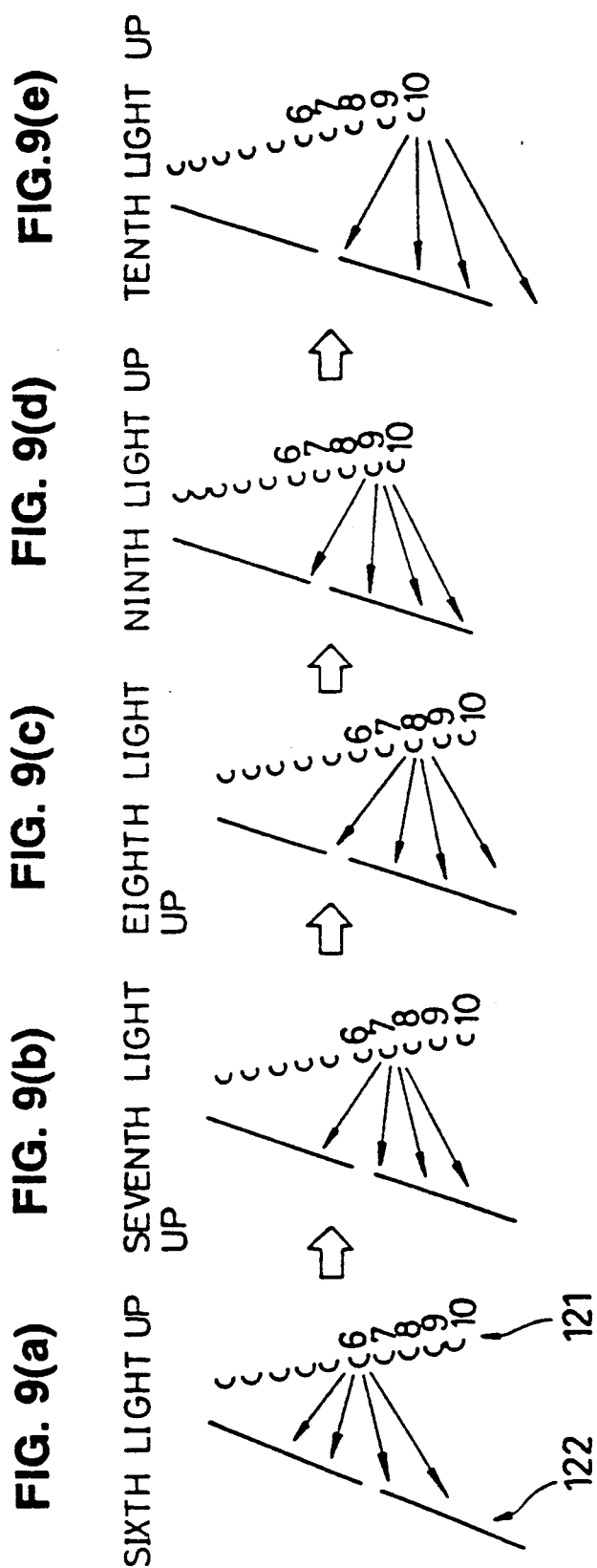

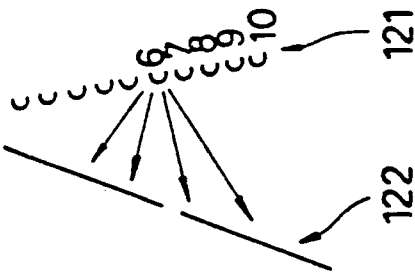
FIG. 10(a) TENTH LIGHT UP
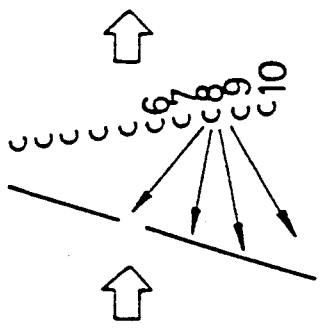
FIG. 10(b) EIGHTH LIGHT UP
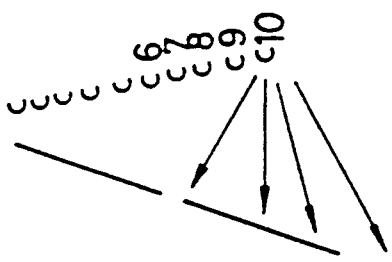
FIG. 10(c) SIXTH LIGHT UP

SOLUTION SEPARATING APPARATUS

BACKGROUND OF THE INVENTION

1. Field of the Invention

This invention relates to a solution separating apparatus, and particularly to a solution separating apparatus for separating blood plasma, red blood corpuscles, etc. from a flexible container such as a blood bag.

2. Prior Art

Since an evil effect of a total blood transfusion has heretofore been regarded as a big issue, a blood transfusion of only blood component is popularly performed at present for the purpose of minimizing, as much as possible, a side effect caused by physical burden to patients, immunity, etc. by performing a blood transfusion of only a blood component or components necessary for patients among various kinds of blood components. As a consequence, it is required to prepare a component formulation, and in order to prepare a component formulation, it is further required that blood in a blood bag is divided into each component by a centrifugal separator, and each component is separated in a separation bag.

An apparatus for separating blood in such a blood bag into each component is disclosed in Japanese Patent Early Laid-open Publication No. Sho 63-119776.

PROBLEMS TO BE OVERCOME BY THE INVENTION (A) That is, the conventional solution separating apparatus includes a plurality of container holding portions for holding a plurality of containers connected by tubes, a plurality of tube clampers for clamping the tubes communicating with the respective containers, a container pressurizing portion for accommodating solution which is divided into layers, pressuring the flexible containers held by the container holding portions and pushing out a part of solution in the containers for separation, an interface detecting portion for detecting the interface of the divided solution in each container, an interface setting portion for setting an interface setting position relative to the container, and a control unit for controlling the tube clampers and the container pressurizing portion, making it possible to transfer solution between the containers communicating with each other through the container to be pressurized by the container pressurizing portion and the tubes which are released from being clamped, and clamping the tubes through the tube clampers by recognizing a fact that the interface detected by the interface detecting portion has reached the interface setting position based on the result set by the interface setting portion and the result detected by the interface detecting portion.

The conventional interface detecting portion comprises a light emitting element disposed to one side and a light receiving element disposed to the other side with the container, which is held by the container holding portion, sandwiched therebetween, the light emitting element and light receiving element being set in predetermined position along the interface moving direction within the container and the interface being detected by change in quantity of light transmitted caused by difference in component of the solution contained in the container.

Furthermore, the conventional interface detecting portion is designed such that the set position of the light emitting element and light receiving element can be adjusted in the interface moving direction within the container by means of operation of a control handle or the like. Owing to the foregoing arrangement, the setting of the interface detecting position is changed depending on difference in kind of the bag and a method of separation.

However, in the prior art, the setting of the interface detecting position by the light emitting element and light receiving element is changed by operating the control handle and moving these elements. Accordingly, operating performance is inferior, and the apparatus is complicated and tends to become large in size.

An object of the present invention is to simplify and miniaturize an apparatus and making it easy to change the setting of a solution interface, so that it will be convenient when a solution interface in a container, which is supposed to be at the end of separating operation, is set to a predetermined position at the time each component of the solution divided in a container is separated, and the timing for the interface detected by an interface detecting portion to reach the set interface position is recognized.

(B) Also, the conventional solution separating apparatus includes a plurality of container holding portions for holding a parent bag and a plurality of child bags connected by a tube, a plurality of tube clampers for clamping tubes communicating with the respective bags, a container pressurizing portion for pressurizing the parent bag held by the container holding portion and pushing out a portion of solution in the parent bag for separation, a measuring portion such as a weight disposed to a container holding portion for each child bag, and control units for controlling the tube clampers and the container pressurizing portion and making it possible to transfer solution to be separated from the parent bag to the child bags which are in communicated relation through the unclamped tubes. And the control unit causes the corresponding tube clamper to clamp the tube communicating with the child bag when the quantity of solution transferred to the child bag from the parent bag has reached a preset level and then finishes the separating operation.

The weight measuring portion of the solution separating apparatus disposed in each container holding portion for each child bag as mentioned above have the following functions ①~③.

① To measure the quantity of blood and additive solution transferred from the parent bag and other child bags.

② To measure the quantity of blood and additive solution transferred to the parent bag and other child bags.

③ To measure the weight of bags for judging whether the bags set to the respective container pressurizing portions are coincident with bags preliminarily selected by a bag selection button or the like.

However, in the conventional solution separating apparatus, since a separate weight measuring portion is required for each container holding portion for each child bag, it has the following problems ① and ②.

① Since a certain scale of weight measuring portion is required for each container holding portion, the apparatus inevitably becomes complicated and large.

② It is difficult to equalize the measuring accuracy of each weight measuring portion, and irregularities in weight measuring results in respective container holding portions are inevitably produced per each weight measuring portion.

It is therefore an object of the present invention that a solution separating work is performed using a plurality of containers connected with each other through tubes, the apparatus is simplified and miniaturized when amount of weight change of each container is measured, and irregularities in weight measuring results in the respective container holding portions are prevented from occurring.

SUMMARY OF THE INVENTION

A solution separating apparatus in accordance with one aspect of the invention includes a container holding portion for holding a container, a container pressurizing portion for containing solution divided into layers, pressurizing a flexible container held by the container holding portion, and pushing out a portion of the solution contained in the container for separation, an interface detecting portion for detecting an interface of the solution divided in the container, an interface setting portion for setting an interface setting position for the container, and a control unit capable of recognizing a fact that the interface detected by the interface detecting portion has reached the interface setting position in accordance with a result set by the interface setting portion and a result detected by the interface detecting portion, the interface detecting portion comprises a light emitting apparatus disposed to one side and a light receiving apparatus disposed to the other side with the container held by the container holding portion sandwiched therebetween, the light emitting apparatus comprises a plurality of light emitting elements disposed in parallel in the substantially moving direction of the interface within the container.

A solution separating apparatus in accordance with another aspect of the invention includes a plurality of container holding portions for holding a plurality of containers connected with each other by tubes, a plurality of tube clampers for clamping the tubes communicating with the respective containers, a container pressurizing portion for containing solution divided into layers, pressurizing a flexible container held by the container holding portion, and pushing out a portion of the solution contained in the container for separation, an interface detecting portion for detecting an interface of the solution divided in the container, an interface setting portion for setting an interface setting position for the container, and a control unit for controlling the tube clampers and the container pressurizing portion so as to make it possible to transfer solution between the container pressurized by the container pressurizing portion and containers communicated with each other through unclamped tubes and clamping the tubes through the tube clampers by recognizing a fact that the interface detected by the interface detecting portion has reached the interface setting position in accordance with a result set by the interface setting portion and a result detected by the interface detecting portion, the interface detecting portion comprises a light emitting apparatus disposed to one side and a light receiving apparatus disposed to the other side with the container held by the container holding portion sandwiched therebetween, the light emitting apparatus comprises a plurality of light emitting elements disposed in parallel in the substantially moving direction of the interface within the container.

In accordance with another feature of the invention the control unit includes a memory portion for storing the position set by the interface setting portion, the memory portion is capable of rewriting and reading the stored data, the stored data is not lost even when a main electric power source is cut off.

In accordance with another feature of the invention, the light receiving apparatus comprises a plate-like light receiving element.

In accordance with yet another feature of the invention, the control unit controls such that the position for detecting operation of the interface detecting portion corresponds to the interface setting position set for the container of this time, a main light emitting element located in the detection operation position, and an upper light emitting element and a lower light emitting element which are located in an upper side and a lower side of the detecting operation position are repeatedly emitted in sequence, light receiving quantities of the light receiving apparatus at the light emitting timing of the light emitting elements are found as a main light receiving quantity, an upper light receiving quantity and a lower light receiving quantity, the control unit recognizes that the interface in the container has reached the interface set position under the conditions that the primary light receiving quantity came to be generally coincident with ½ of a difference between the upper light receiving quantity and the lower light receiving quantity.

In accordance with still another feature of the invention the control unit controls such that the position for detecting operation of the interface detecting portion corresponds to the interface setting position set for the container of this time, a main light emitting element located in the detection operation position, and an upper light emitting element and a lower light emitting element which are located in an upper side and a lower side of the detecting operation position are repeatedly emitted in sequence, light receiving quantities of the light receiving apparatus at the light emitting timing of the light emitting elements are found as a main light receiving quantity, an upper light receiving quantity and a lower light receiving quantity, the control unit recognizes that the interface in the container has reached the interface set position under the conditions that a difference between the primary light receiving quantity and the lower light receiving quantity exceeds a reference level.

In accordance with another feature of the invention, the light emitting elements are infrared light emitting elements, a visible light emitting element is juxtaposed to each of the light emitting elements.

In accordance with another feature of the invention, is that the infrared light emitting elements are connected in series to corresponding visible light emitting elements on an electric circuit.

According to the invention, the following function and effect ① is resulted.

① As it includes a plurality of light emitting elements disposed, in parallel relation, in the substantially interface moving direction in a container, change in transmission light quantity can be observed at a plurality of places along the interface moving direction in the container by absolutely evaluating the light receiving quantity of the light receiving apparatus corresponding to each light emitting element or by relatively evaluating it among the light emitting elements. As a result, the apparatus can be simplified and miniaturized and the setting of solution interface in the container can be changed with ease, without a provision of a mechanism for moving the light emitting elements and light receiving elements.

Among detecting methods of the present invention by an interface detecting portion, an absolute value detecting method will be described.

First of all, the control unit causes, for example, first to fifteenth light emitting elements constituting a light emitting apparatus of the interface detecting portion to light up orderly and repeatedly as soon as the separating operation is started. At the same time, the control unit detects a fact that the interface in the container has reached position corresponding to the light emitting element when it is transferred light receiving quantity of light receiving elements constituting the light receiving apparatus or when a light receiving quantity corresponding to a certain light emitting element has reduced to a predetermined level. By this, the control unit can recognize that the interface detected by the interface detecting portion has reached the interface set position.

According to a feature of the invention the following function and effect ② is obtained.

② The set position by the interface setting portion can be adjusted by rewriting data stored in a memory portion, the setting can be easily changed, and each component of the solution can be separated with high accuracy in such a manner as to correspond to the difference in kind of containers and method of separation. At this time, the set interface position stored in the memory portion is not erased even when a main electric power source is abruptly cut off by a power failure, etc., and the same set interface position is maintained repeatedly unless it is rewritten.

According to another feature of the invention the following function and effect ③ is obtained.

③ As the light receiving apparatus is formed of a plate-like light receiving element, it becomes compact and the apparatus can be miniaturized.

According to still another feature of the invention the following function and effect ④ is obtained.

④ In the absolute value detecting method mentioned in the above ①, the light receiving quantity served as a reference as to whether the interface is present or not is a predetermined fixed level. On the contrary, the method of the present invention is a relative value detecting method in which light receiving levels corresponding to the light emitting timing for the adjacent light emitting elements are compared with each other. Therefore, the following functions and effects (a)~(c) are obtained.

(a) Strong resistance against dirt or stain of the light emitting element and light receiving element.

(b) Strong against aging change of the light emitting element and light receiving element.

(c) Adverse effects from disturbance light can be canceled (When the electric power source is activated, the disturbance light can be corrected, and it can likewise cope with a case where the level of disturbance light, while in use, is changed with the passage of time such as from day to night or from night to day).

According to yet another feature of the following function and effect ⑤ is obtained.

⑤ Detection sensibility can be enhanced by using an infrared light emitting element as the light emitting element for the use of interface detection. It is noted, however, that the infrared light emitting element is not a visible light and therefore, it cannot be recognized by sight even if it is lighted up.

Therefore, by using the infrared light emitting element together with the visible light emitting element and lighting them up simultaneously, the following functions and effects (a)~(b) are obtained.

(a) When a detected position is set, by lightening the set position, it becomes easy to recognize by sense.

(b) It can be recognized by sight whether the set position is correct or not.

(c) As the visible light emitting element is lighted up during action, it can be know as to whether the action is normally performed.

According to still another feature of the invention the following function and effect ⑥ is obtained.

⑥ By connecting the infrared light emitting element for the use of detecting the interface with the visible light emitting element in series and lightening up, trouble of these elements can be found. Either the infrared light emitting element or the visible light emitting element gets out of order, it is not lighted up electrically.

(B) A solution separating apparatus in accordance with the invention may also include a plurality of container holding portions for holding a plurality of containers connected with each other by tubes, a plurality of tube clampers for clamping the tubes communicating with the respective containers, a container pressurizing portion disposed in such a manner as to correspond to at least one container holding portion and adapted to pressurize a flexible container held by the container holding portion and push out a portion of solution contained in the container for separation, and a control unit for controlling the tube clampers and the container pressurizing portion, the control unit making it possible to transmit solution between containers communicated with each other through unclamped tubes, the solution separating apparatus further includes a weight measuring portion which is commonly had by two or more container holding portions, quantities of weight change of the respective containers held by the container holding portions are able to be selectively measured.

In a solution separating apparatus in accordance with another feature of the invention, the control unit is capable of obtaining the result measured by the weight measuring portion and recognizes the container holding portion for holding containers which are communicated with unclamped tube this time, the control unit further is capable of calculating the quantities of weight change of the containers held by the container holding portion from a result of measurement obtained by the weight measuring portion.

A solution separating apparatus in accordance with another feature of the invention which further includes a solution quantity setting portion for setting a solution quantity which should be contained in the containers, and a memory portion for storing the set solution quantity, the memory portion is capable of rewriting and reading the stored data, the stored data is not lost even if the main electric power source is cut off, the control unit recognizes that the solution quantity in the corresponding container has reached the set solution quantity in accordance with the data of set solution quantity stored in the memory portion and the result of measurement obtained by the weight measuring portion, and clamps the tube communicating with the container through the corresponding tube clamper.

According to still another feature of the invention the following functions and effects ⑦ and ⑧ are obtained.

⑦ Since a plurality of container holding portions commonly have a single weight measuring portion, the apparatus can be simplified and miniaturized when the amount of weight change for each container is measured.

⑧ The result of weight measurement of each container holding portion is a result measured by the same weight measuring portion, and no irregularities caused by different weight measuring portions are generated.

According to a feature of the invention the following function and effect ⑨ is obtained.

⑨ The control unit recognizes the container which is to be changed in weight this time from the unclamped state of the tube and is capable of selectively measuring the quantity of change in weight of the container held by the container holding portion which participates in the separating work this time among a plurality of container holding portions which are under the control of the weight measuring portion.

According to another feature of the invention the following function and effect 10 is obtained.

10 The set solution quantity to be accommodated in each container can be constituted by rewriting the data stored in the memory portion, the setting can be easily changed, and each component of the solution can be accurately separated into each container. At this time, the set solution quantity stored in the memory portion is not erased even when the main electric power source is cut off by power failure or the like, and the same set solution quantity is maintained repeatedly unless the same is rewritten.

BRIEF DESCRIPTION OF THE DRAWINGS

FIGS. 9(a)-(e) are schematic views showing the sequential steps of light emission of the light emitting apparatus;

FIGS. 10(a)-(c) are schematic views showing other sequential steps of light emission of the light emitting apparatus;

DETAILED DESCRIPTION OF THE INVENTION

Figure 1:
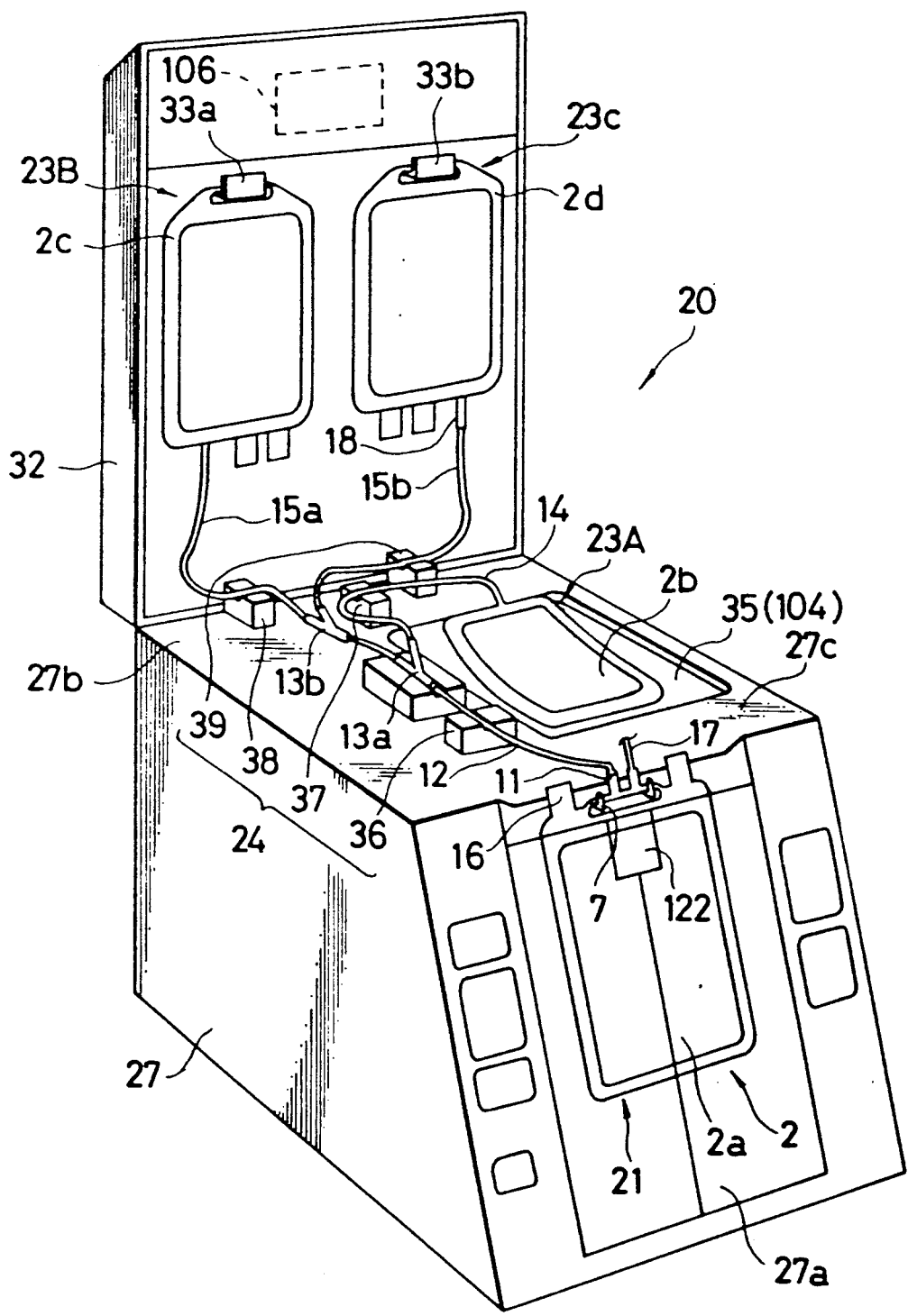
FIG. 1 is a perspective view showing one embodiment of a solution separating apparatus.
Figure 2:
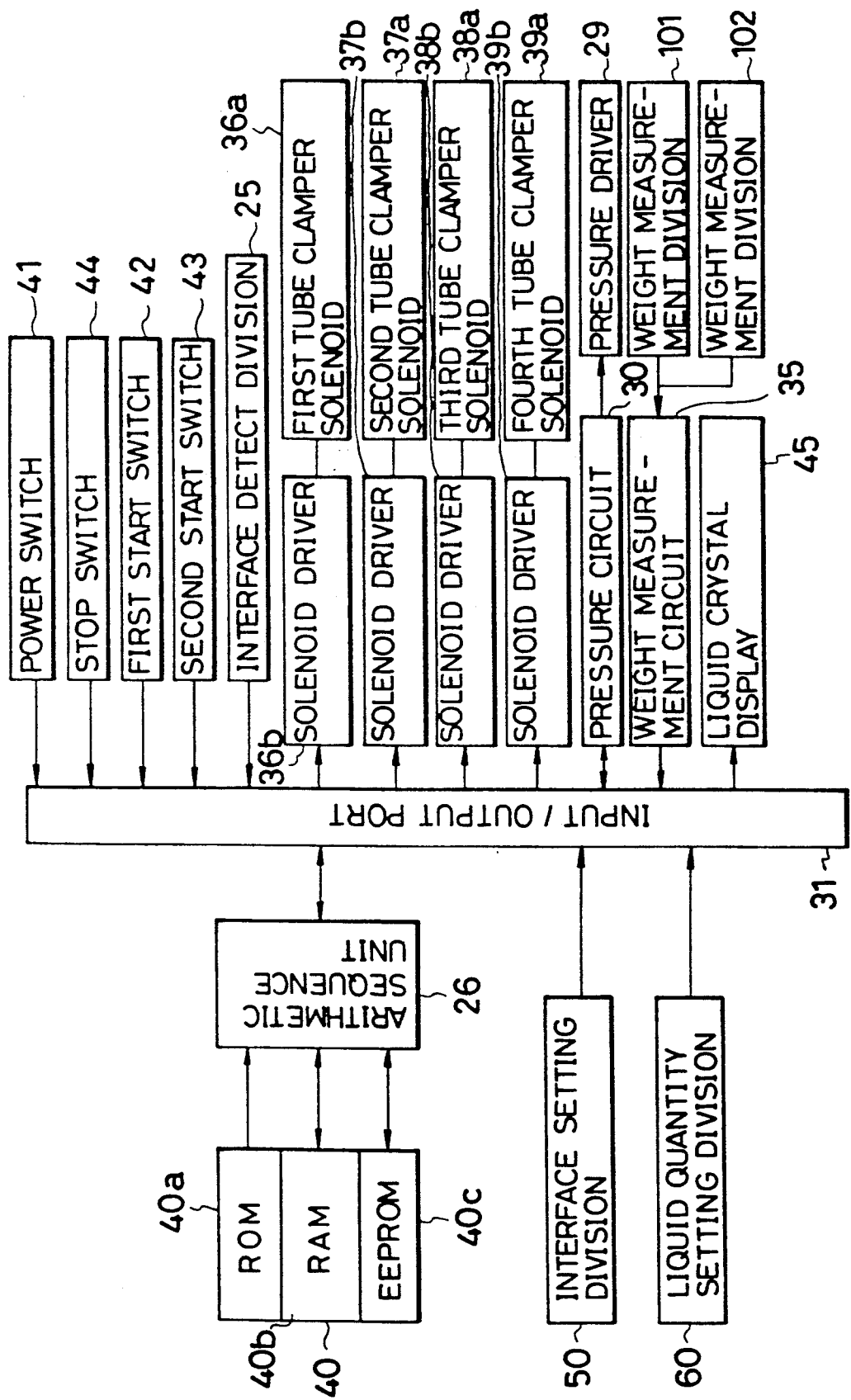
FIG. 2 is a block diagram showing a control system of the solution separating apparatus.

A solution separating apparatus 20 is chiefly used for separating components of blood and its objective blood bag 2 is for 200 ml and 400 ml, and a double bag, a triple bag, and red blood corpuscle removing quadruple bag (additive solution is present or not present) can be used. In this embodiment, a leukocyte removing quadruple bag for 400 ml is used.

The automatic solution separating apparatus 20 chiefly comprises a main container holding portion 21 (see FIG. 3) for holding a parent bag 2a provided with a solution taking off tube 11, a container pressurizing portion 22 for pressuring the parent bag 2a held by the main container holding portion 21 and pushing out a blood component in an upper layer within the parent bag 2a, first through third secondary container holding portions 23A~23C for holding first, second and third child bags 2b, 2c and 2d for containing the blood component in the upper layer pushed out from a solution take-off tube 11 of the parent bag 2a by the container pressurizing portion 22 through tubes, a shutter member 24 for opening and closing each tube, an interface detecting portion 25 for detecting the interface of blood contained in the blood bag 2, weight measuring portions 101 and 102 for measuring the weight of blood components contained in the respective child bags 2b, 2c and 2d, and an arithmetic sequence unit (or control unit) 26 for calculating detection signals detected by the interface detecting portion 25, measurement signals measured by the weight measuring portions 101 and 102, and operation signals for operating the container pressurizing portions 22 and the shutter portion 24 in accordance with a program initially input and outputting the same.

Figure 3:
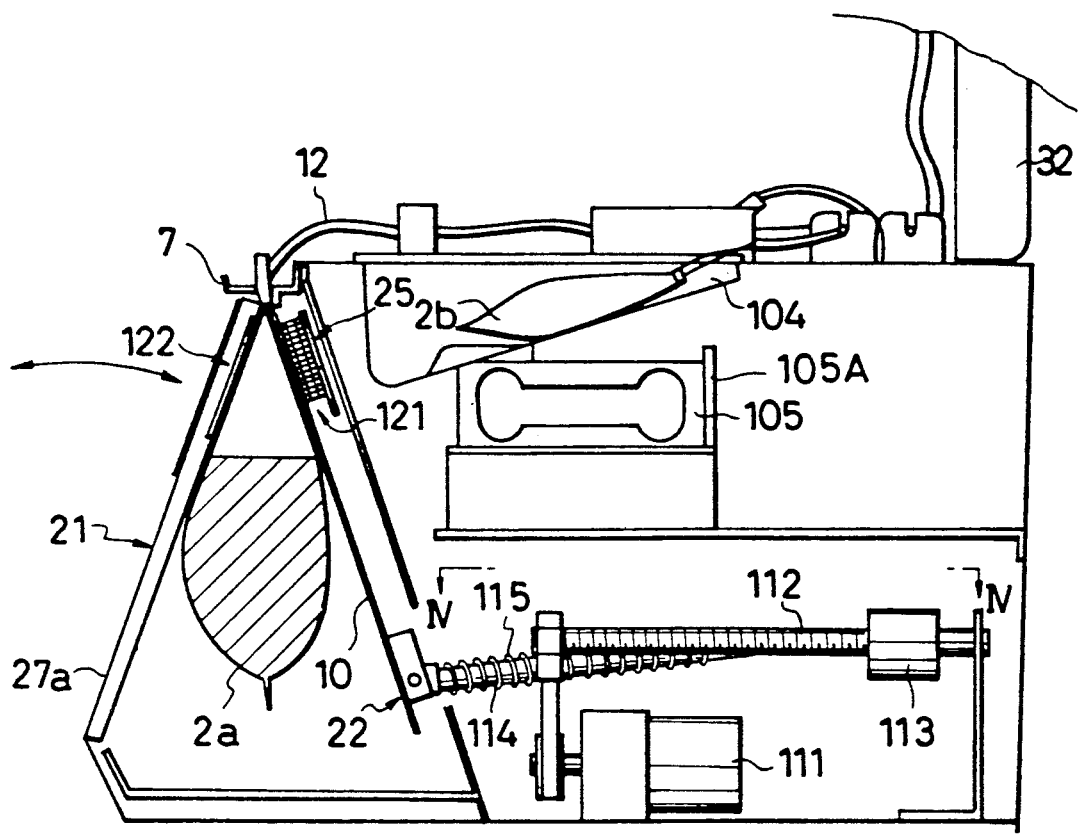
FIG. 3 is a sectional view showing an important portion of FIG. 1.
Figure 4:
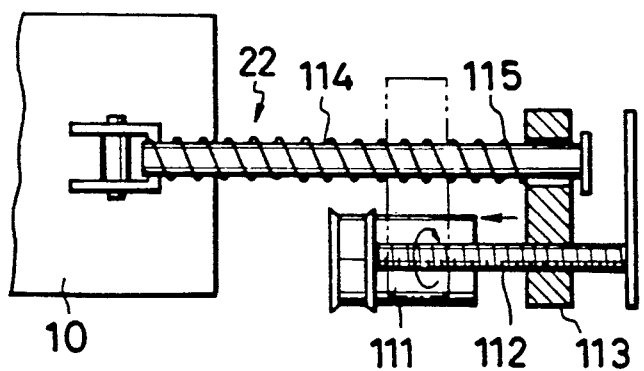
FIG. 4 is a sectional view taken on line IV—IV of FIG. 3.

The main container holding portion 21 is located at a front surface 27a of an operating box 27. The main container holding portion 21, as shown by an arrow in FIG. 3, can be opened and closed. When the main container holding portion 21 is opened, the parent bag 2a is hooked on the hooks 7, 7 and when it is closed, it looks as shown in FIG. 3.

Figure 5:
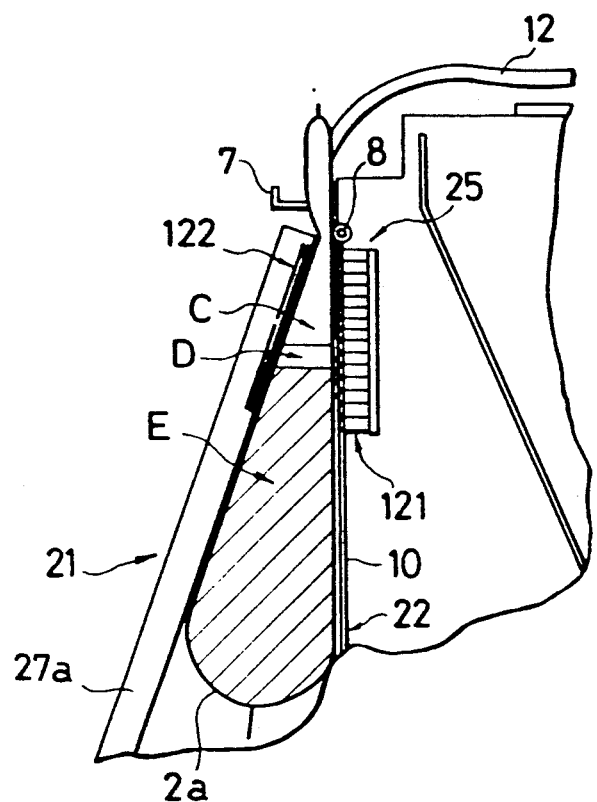
FIG. 5 is a sectional view showing a pressurizing state of a container.

The container pressurizing portion 22 is designed such that a pressure plate 10 fixed to a rotational shaft 8 supported by the operating box 27 is pushed toward the container holding portion 21 side by a pushing mechanism and the parent bag 2a is sandwiched, under pressure, between the pressure plate 10 and the container holding portion 21 (see FIG. 5). The pushing mechanism is constructed as shown in FIG. 3. The numeral 111 denotes a motor, 112 a feed screw shaft, 113 a movable piece, 114 a mandrel, and 115 a spring. The feed screw shaft 112 is driven by the motor 111, and the movable piece 113 is engaged with the feed screw shaft 112 through the screw means and moved in the axial direction of the feed screw shaft 112. The mandrel 114 is connected to the pressure plate 10 by pin means and loosely engaged with the movable piece 113. The spring 115 is mounted on the periphery of the mandrel 114 and is biased by the movable piece 113. Accordingly, ① when the arithmetic sequence unit 26 rotates the motor 111 in the normal direction through a pressure circuit 30, the feed screw shaft 112 is rotated and the movable piece 113 is moved in the axial direction of the shaft 112. ② The movable piece 113 simultaneously biases the spring 115 and stops at the end of its advancement. ③ By this, the biased spring 115 gradually urges the pressure plate 10 into a pivotal movement as mentioned above.

The solution separating apparatus 20 has a cover 32 mounted on an upper surface 27b of the operating box 27 in such a manner as to be opened and closed. This cover 32 can be fixed to the upper surface 27b in the vertical direction and is provided with a couple of hooks 33a and 33b so that two child bags can be hung thereon. Furthermore, an upper surface 27b of the operating box 27 is provided with a tray 35 on which a single child bag can be placed.

The shutter portion 24 comprises first, second, third and fourth tube clampers 36, 37, 38 and 39 which are disposed on the upper surface 27b of the operating box 27, the tube clampers 36, 37, 38 and 39 being opened and closed by corresponding solenoids 36a, 37a, 38a, and 39a, respectively.

The solenoids 36a, 37a, 38a and 39a are electrically connected to the arithmetic sequence unit 26 through drivers 36b, 37b, 38b and 39b, and an input/output port 31.

The interface detecting portion 25 is adapted to detect an interface between a blood plasma layer C and a mucosa layer D of the blood bag 2 which was already subjected to centrifugal separation treatment, and/or an interface between the mucosa layer D and a red blood corpuscle E, and a photosensor is used for it in general, the interface being detected by difference in light absorption coefficient in respective layers. The mounting position of this interface detecting portion 25 can be slightly amended in the vertical direction. This interface detecting portion 26 is electrically connected to the arithmetic sequence unit 26 through the input/output port 31.

Figure 8A:
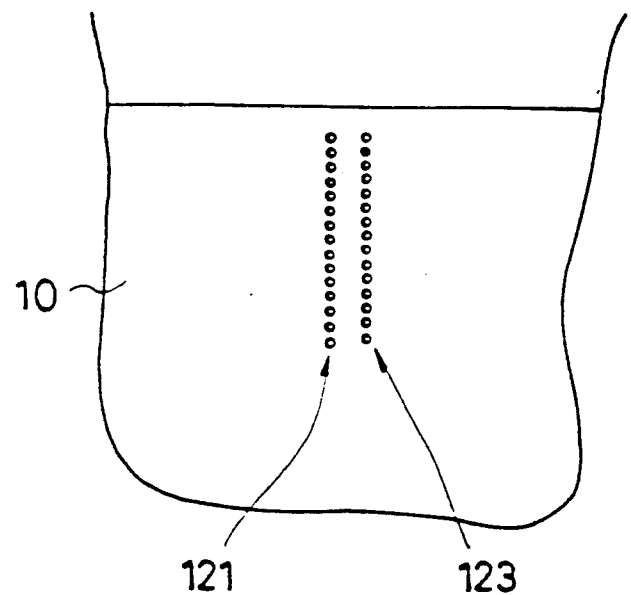
FIGS. 8(a) and 8(b) are schematic views showing a light emitting apparatus and a light receiving apparatus.
Figure 8B:
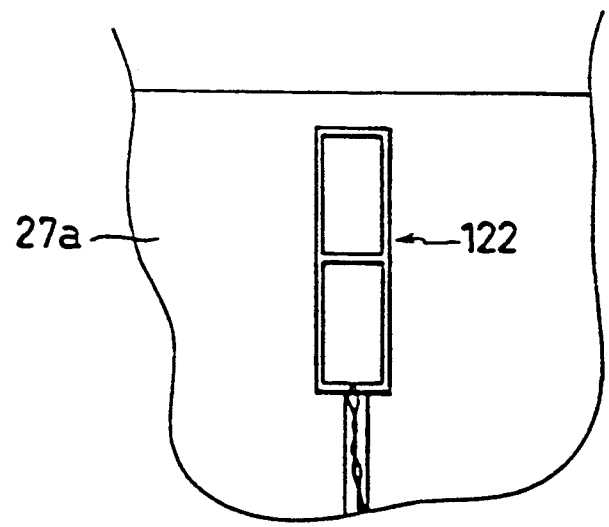

This interface detecting portion 25 is concretely constructed as shown, for example, in FIGS. 5 and 8. That is, in FIGS. 5 and 8, the numeral 121 denotes a light emitting device disposed at the pressure plate 10, and 122 a light receiving device disposed at a side surface 27a of the operating box 27. The light emitting apparatus 121 comprises 15 pieces of first through fifteen infrared light emitting diodes disposed long in the vertical direction of the blood bag 2 set in the main container holding portion 21, and the light receiving apparatus 122 comprises two plate-like light emitting diodes connected in parallel.

At this time, the solution separating apparatus 20 includes an interface setting portion 50 for setting an interface setting position (required position of the interface at the time the separating work has been finished) relative to the blood bag 2 set to the main container holding portion 21 in accordance with a quantity of blood plasma which should be remained in the blood bag 2 at the time the separating work has been finished this time (accordingly, in accordance with the capacity of the blood bag 2 which is used this time, or in accordance with the conditions of the centrifugal separation in the preceding process). Also, the solution separating apparatus 20 is adapted to store the interface set position set by this interface setting portion 50 in a non-volatile EEPROM 40c of a memory portion 40 which will be described later. The non-volatile EEPROM 40c is capable of rewriting and accessing the stored data and these data are not erased even when the main electric power source is cut off.

The sequence unit 26 calculates the quantity of the light receiving diode of a light receiving apparatus 122 corresponding to each light emitting diode of the light emitting apparatus 121 in the following manner.

Figure 11:
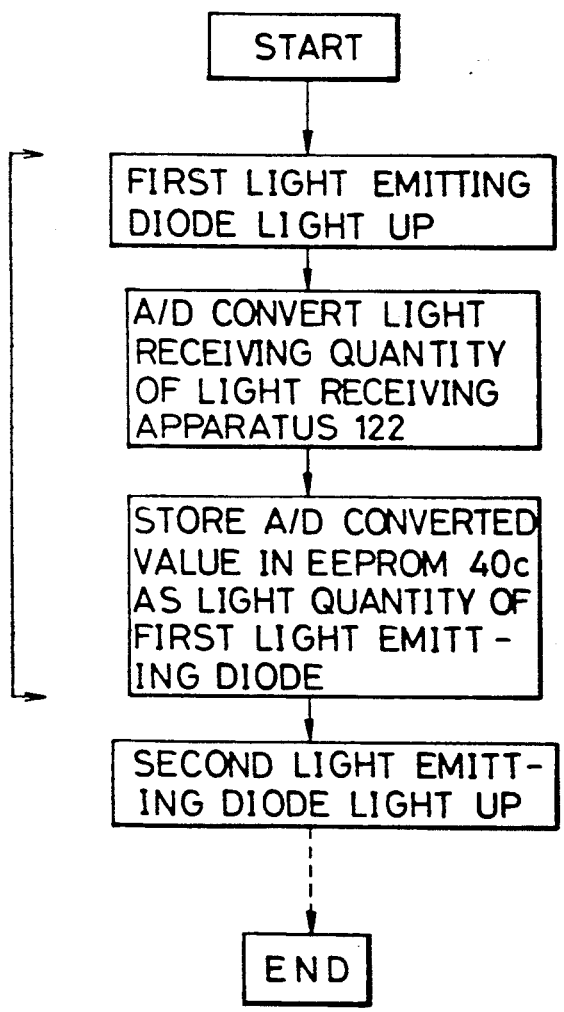
FIG. 11 is a flowchart showing a correction action when the light emitting element is assembled.

(1) Calibration of Light Emitting Diode at Assembling Time (see FIG. 11)

Since the intensity of each light emitting diode is irregular, the first through fifteen light emitting diodes, as shown in FIG. 11, are lighted up in sequence and the light receiving quantity of the corresponding light receiving apparatus 112 is stored in the EEPROM 40c on the assembling and adjusting stage wherein the blood bags 2 are not attached to the solution separating apparatus 20.

What the EEPROM 40c actually stores as data is not an A/D converted value (actual value) of the light receiving quantity but the following coefficient of correction. That is, the sequence unit 26 calculates about what % the intensity of each light emitting element is in a certain value and stores the same as a coefficient of correction. Presuming the certain value (reference value) is 100, if the A/D value of the light intensity of the first light emitting diode is 90, the coefficient of correction thereof is 100/90, if the A/D value of the light intensity of the second light emitting diode is 120, the coefficient of correction thereof is 100/120, and if the A/D value of the light intensity of the third light emitting diode is 100, the coefficient of correction thereof is 100/100.

Figure 12:
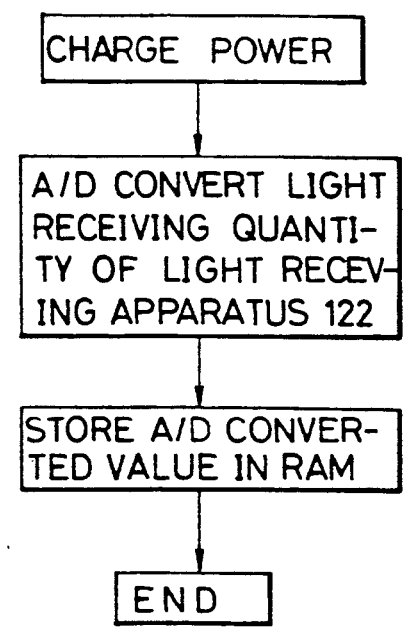
FIG. 12 is a flowchart showing a correction action for intensity of disturbance light when an electric power source of the light emitting element is charged.

(2) Calibration of Intensity of Disturbance Light at Electric Power Source Charging Time (FIG. 12)

Since intensity of disturbance light (illumination, window, etc.) is different depending on the circumstance under which the solution separating apparatus 20 is used, the light receiving quantity of the light receiving apparatus 122 at the electric power source charging time is stored in RAM as intensity of disturbance light as shown in FIG. 12.

(3) Correcting Calculation of Light Receiving Quantity

When the coefficients of correction found by the above (1) for the respective light emitting diodes are represented by $A_1 \ldots A_{15}$, and the intensity of disturbance light (A/D converted value) found by the above (2) is represented by B, if the A/D converted values of the light receiving quantity of the light receiving apparatus 122 at the time the respective light emitting diodes are lighted up are represented by $X_1 \ldots X_{15}$, the calculated light receiving quantities $Y_1 \ldots Y_{15}$ of the respective light emitting diodes can be calculated from the following equation;

$$Y_n = A_n \times (X_n - B) \qquad (1).$$

As a method for the interface detecting portion 25 to detect an interface position set by the interface setting portion 50, there are the following methods (A), (B) and (C).

(A) ABSOLUTE VALUE DETECTING METHOD

① Upon start of the separating operation, the sequence unit 26 causes the first through fifteenth light emitting diodes constituting the light emitting apparatus 121 of the interface detecting portion 25 to be lighted up repeatedly in sequence. At the same time, the sequence unit 26 is transferred the light receiving quantities of the light receiving diodes constituting the light receiving apparatus 122 after they are A/D converted, and detects a fact that when a light receiving quantity corresponding to a certain light emitting diode is reduced to a predetermined level, the interface within the blood bag reaches a position corresponding to the light emitting diode.

② By this, the control units 26 receives the set data of the interface setting portion 50 stored in the non-volatile EEPROM 40c and the result detected by the interface detecting portion 25, and recognizes from the foregoing that the surface detected by the interface detecting portion 25 has reached the interface set position.

Figure 13:
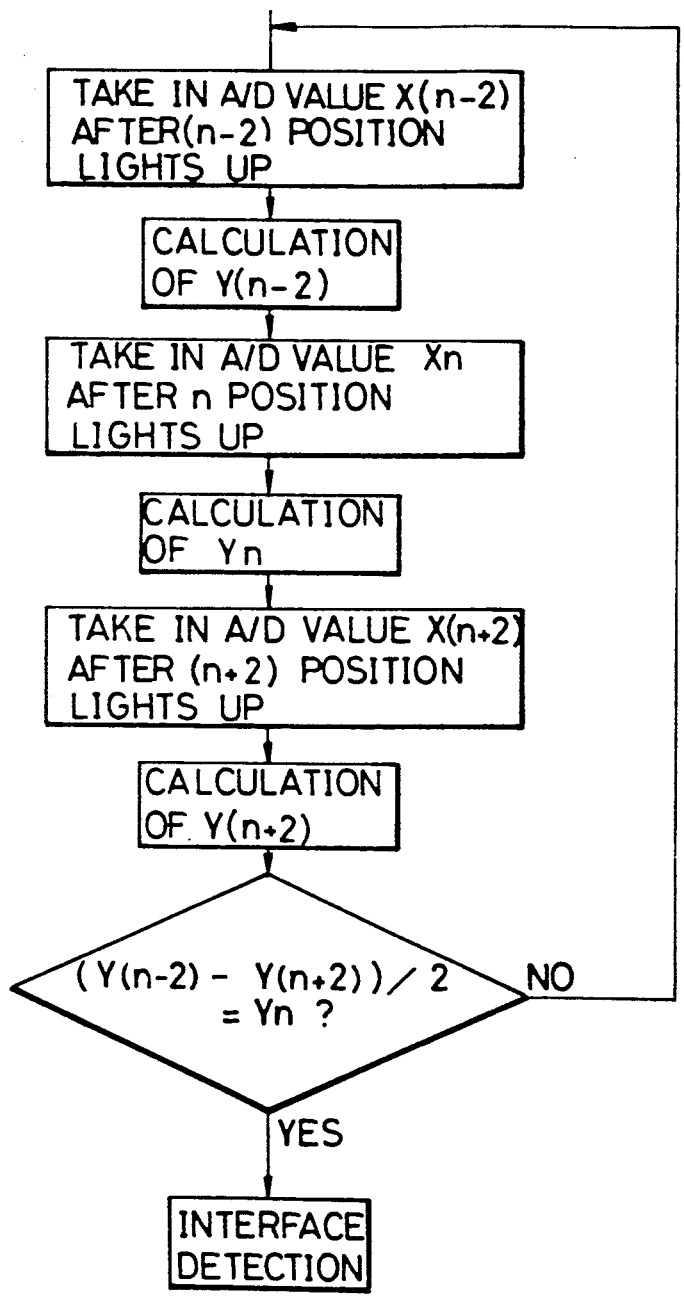
FIG. 13 is a flowchart showing the interface detecting action by the interface detecting portion.

(B) RELATIVE VALUE DETECTING METHOD—1 (see FIG. 13)

① The sequence unit 26 adjusts the detecting work position of the interface detecting portion 25 in such a manner as to correspond to the interface set position which has been set relative to the blood bag 2 of this time in accordance with the data of the interface setting portion 50 stored in the non-volatile EEPROM 40c.

② However, if the set position of the interface setting portion 50 is decided to a position corresponding to, for example, the eighth light emitting diode (main light emitting element), the sequence unit 26, upon start of the separating operation, causes the five pieces of elements of the interface diode (lower light emitting element) to be repeatedly lighted up from up to down (or from down to up) in sequence as shown in FIG. 9.

③ At the same time, the sequence unit 26 intakes a light receiving quantity $X_6$ of the light receiving apparatus 122 corresponding to the sixth light emitting diode and finds a calculation light receiving quantity $Y_6$ (upper light receiving quantity) after correction. Likewise, the sequence unit 26 finds a calculation light receiving quantity $Y_6$ (main light receiving quantity) corresponding to the eighth light emitting diode and a calculation light receiving quantity $Y_{10}$ (lower light receiving quantity) corresponding to the tenth light emitting diode.

④ And the sequence unit 26 recognizes that the interface of the blood bag 2 has reached the interface set position when the primary light receiving quantity $Y_8$ came to be generally coincident with $\frac{1}{2}$ of a difference $(Y_6 - Y_{10})$ between the upper light receiving quantity $Y_6$ and the lower light receiving quantity $Y_{10}$, that is, when the following equation is established;

$$Y_n = (Y_{n-2} - Y_{n-2})/2 \quad (2)$$

Figure 14:
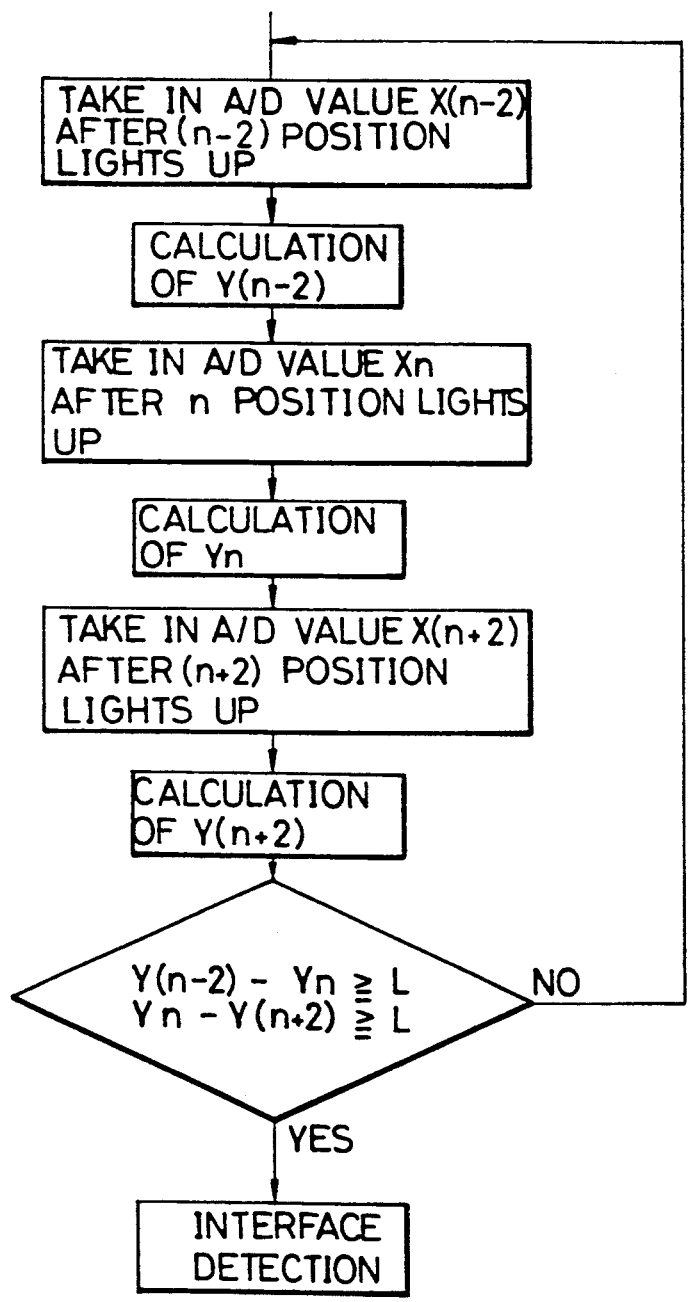
FIG. 14 is a flowchart showing other interface detectingaction by the interface detecting portion.

(C) RELATIVE VALUE DETECTING METHOD-2 (see FIG. 14)

After the main light receiving light quantity $Y_8$, the upper light receiving quantity $Y_6$ and the lower light receiving quantity $Y_{10}$ have been found in the same manner as ①~③ of the above (B), the sequence unit 26 recognizes that the interface of the blood bag 2 has reached the interface set position when a difference between the main light receiving quantity $Y_8$ and the upper light receiving quantity $Y_6$ came to a reference level L or more, or a difference between the main light receiving quantity $Y_8$ and the lower light receiving quantity $Y_{10}$ came to a reference value L or more (OR condition), that is, when the following expressions are established;

$$T_{n-2} - Y_n \geq L \quad (3)$$

$$Y_n - Y_{n-2} \geq L \quad (4)$$

In the above (B) and (C), it may be designed such that as shown in FIG. 10, the seventh and ninth light emitting diodes vertically adjacent to the the eighth light emitting diode as a main light emitting element are not lighted up and three pieces of the sixth, eighth and tenth elements are repeatedly lighted up in sequence by serving only the sixth light emitting diode as the upper light emitting element and only the tenth light emitting diode as the lower light emitting element.

If the sequential light emitting direction of the respective light emitting diodes constituting the light emitting apparatus 121 is coincident with the moving direction of the interface within the blood bag, there can be obtained a surplus time for the detection processing. On the other hand, if the sequential light emitting direction is arranged in the opposite way, there is a high probability that it is detected at an upper side (the side toward which the interface advances) than the actual interface set position and thus undesirable.

By the way, in the interface detecting portion 25, the respective light emitting diodes constituting the light emitting apparatus 121 are designed to be infrared light emitting diodes and visible light (for example, red color light) emitting diodes constituting the confirmation display apparatus 123 are juxtaposed to positions adjacent to the respective infrared light emitting diodes (see FIG. 8). The confirmation display apparatus 123 causes a particular visible light emitting diode of the confirmation display apparatus 123 corresponding to the interface detecting position of this time to be lighted up so that this interface set result can be confirmed.

At this time, the interface detecting portion 25 is designed such that the corresponding infrared light emitting diode and visible light emitting diode are connected in series on an electric circuit so that disorder of the diodes can be found. If either the infrared light emitting the diode or the visible light emitting diode gets out of order, none of the diodes is electrically lighted up.

The weight measuring portions 101 and 102 are electrically connected to the arithmetic sequence unit 26 through the weight measuring circuit 35 and the input-/output port 31, and concretely constructed as follows.

The weight measuring portion 101 for the first child bag 2b disposed on the first secondary container holding portion 23A comprises a bag receiving tray 104 for the child bag 2b to be placed thereon, and a weight sensor 105 on which the bag receiving tray 104 is supported, as shown in FIG. 3.

Figure 6:
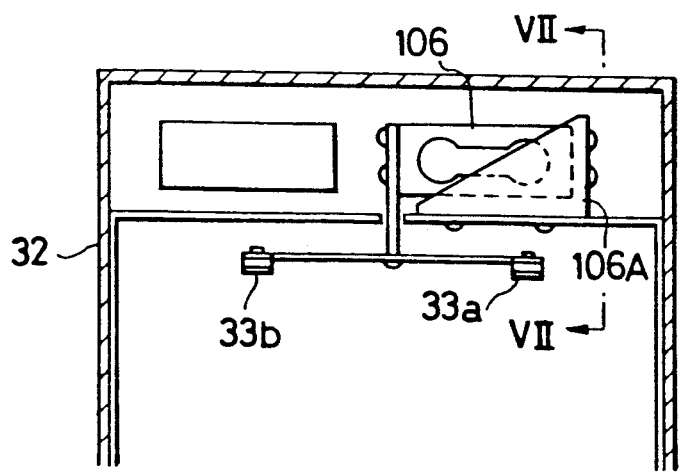
FIG. 6 is a sectional view showing an important portion of FIG. 1.
Figure 7:
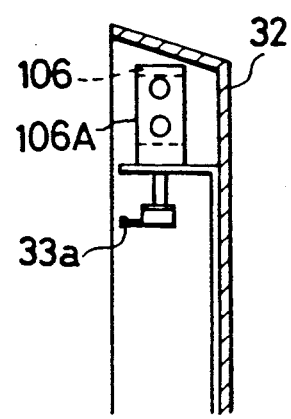
FIG. 7 is a sectional view taken on line VII—VII of FIG. 6.

The weight measuring portion 102 for the child bags 2c and 2d disposed on the second and third secondary container holding portions 23B and 23C comprises hooks 33a and 33b on which the child bags 2c and 2d are hung and a single weight sensor 106 on which the hooks 33a and 33b are supported, as shown in FIGS. 6 and 7. That is, the two container holding portions 23B and 23C commonly have the single weight measuring portion 102 so that the weight changing amounts of the child bags 2c and 2d held in the respective container holding portions 23B and 23C can be selectively measured.

The weight sensors 105 and 16 are supported by sensor holding brackets which are fixed to the operating box 27 and the cover 32 respectively, and include a strain gauge which is attached to two positions of the upper surface and two positions of the lower surface, respectively, to form a Wheatstone bridge circuit.

At this time, the solution separating apparatus 20 includes a solution setting portion 60 for setting the solution quantities which should be contained in the respective child bags 2b~2d set to the first through third secondary container holding portions 23A~23C in accordance with the capacities of the child bags 2b~2d which are used this time. Also, the solution separating apparatus 20 stores the solution quantity set by this solution quantity setting portion 60 in a non-volatile EEPROM 40c which will be described later. The memory portion 40 is capable of rewriting and reading the stored data and the stored data are not erased even when a main electric power source is cut off.

Therefore, the respective weight measuring portions 101 and 102 measure the solution quantity set by the solution setting portion 60 as follows. That is, the arithmetic sequence unit 26 can recognize a fact that the measured results of the respective weight measuring portions 101 and 102 have reached those set solution quantities by obtaining the data of the solution setting portion 60 stored in the non-volatile EEPROM 40c and the measured results of the respective weight measuring portions 101 and 102.

At this time, the arithmetic sequence unit 26 selectively recognizes about to which weight changing quantity of the child bags 2c and 2d held by the container holding portion 23B or 23C the output changing quantity of the weight measuring portion 102 commonly had by the second and third secondary container holding portions 23B and 23C corresponds in the following manner. That is, the sequence unit 26 is capable of obtaining the result of measurement made by the weight measuring portion 102, recognizing the child bags 2c and 2d communicating with the tubes 15a and 15b which has been unclamped by the tube clampers 38 and 39 of the shutter portion 24 this time, recognizing that the result of measurement made by the weight measuring portion 102 corresponds to the weight changing quantity of the child bags 2c and 2d communicating with the tubes 15a and 15b which were unclamped, and calculating the weight changed amount of the child bag 2c or 2d and calculates the weight changing quantity of the child bags 2c or 2d and outputting the same.

The arithmetic sequence unit 26 is adapted to calculate based on signals input from the input/output port 31 and information read from the memory portion 40 (including ROM 40a, RAM 40b, AND EEPROM 40c) according to necessity and to output operating signals to various devices through respective circuits. And a program, in which an operating method of the present invention is initially stored, is loaded in the ROM 40a of the memory portion 40 which is electrically connected to the arithmetic sequence unit 26. This program is well prepared for, for example, a case of 400 ml, a case of 200 ml, and various other cases of various kinds of operation methods, and the operating method can be changed in many ways by selecting this program through the selection switch. The program to be loaded in the ROM 40a may be of the type for exchanging a program cassette prepared for each operating method.

The term "ROM (40a)" refers to a "read only memory" in which a program for automatically performing a solution separating operation is loaded and its content is not lost even when an electric power source is cut off. Also, its content cannot be rewritten.

Likewise, the term "RAM (40b)" refers to a "random access memory" which is a memory adapted to store, in the middle way of the solution separating operation, the current step of separating operation, the result of measurement of the solution quantity, the result of measurement of the interface detecting portion, and the intermediate result of calculation being performed by the arithmetic sequence unit, and its contents are all lost when an electric power source is cut off.

The term "EEPROM (40c)" refers to a "electrical erasable programmable read only memory". Although this is a read only memory, its content can be rewritten by incurring a high voltage for writing. Moreover, the stored content is not lost even when the electric power source is cut off. This EEPROM stores all of the interface detection setting values and solution setting values for each type of blood bags, and the set content can be rewritten only when it is changed to a setting change mode.

That is, the arithmetic sequence unit 26 automatically performs solution separation by operating the container pressurizing portion 22 and shutter portion 24 in accordance with the result detected by the interface detecting portion 25, the result measured by the weight measuring portions 101 and 102, and the program.

At this time, the arithmetic sequence unit 26 closes the shutter portion 24 and finishes the separating operation by recognizing a fact that the interface detected by the interface detecting portion 25 has reached the interface set position and/or the result measured by each weight measuring portion 101, 102 has reached the set solution quantity with reference to the data of the interface set position and set solution quantity stored in the non-volatile EEPROM 40c, the result detected by the interface detecting portion 25, and the result measured by each weight measuring portion 101, 102.

Also, this arithmetic sequence unit 26 is electrically connected with various switches such as a power switch 41, a first start switch 42, a second start switch 43, and a stop switch 44 and a solution crystal display 45. These switches and solution crystal display 45 are attached to a panel portion at an inclined portion 27c of the operating box 27. This solution crystal display 45 is disposed on an operating panel of the operating box 27. And this solution crystal display 45 displays the title of a program to be used. Therefore, it can be made sure whether this program is the right one. Also, error messages such as, for example, interface level and weight meter being abnormal (the child bags are not set in the predetermined places) are displayed on the solution crystal display 45 to that effect.

Next, operation of the automatic solution separating apparatus 20 having the above-mentioned construction will be described.

Figure 15:
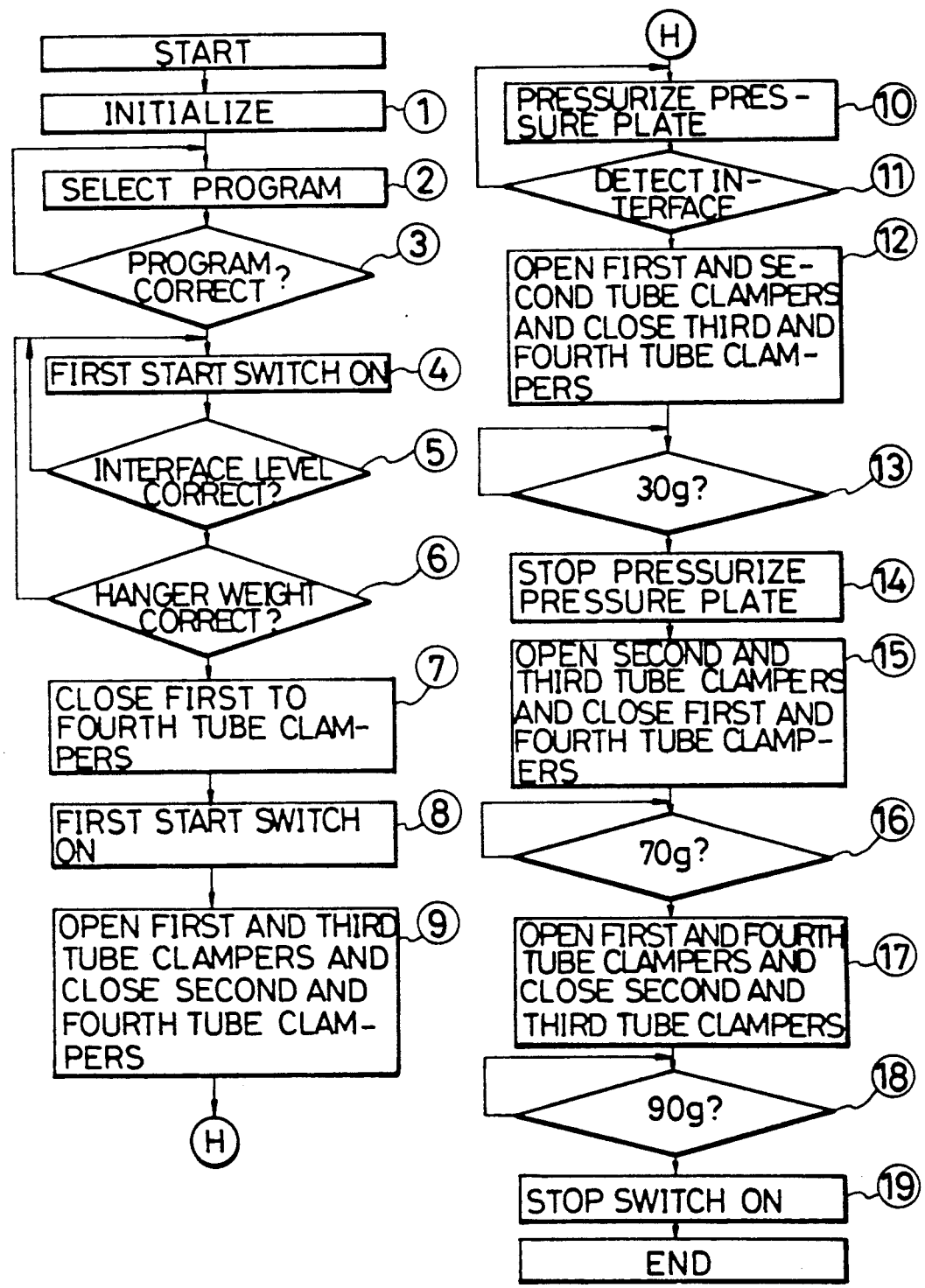
FIG. 15 is a flowchart showing a separating operation using a quadruple bag (additive solution is present) for removing leukocyte.

FIG. 15 is a flowchart showing the operation for a case wherein a quadruple bag (additive solution is present) for removing leukocyte which has been subjected to the first centrifugal separation treatment is used as the solution separating apparatus.

First of all, the electric power switch 41 of the automatic solution separating apparatus 20 is turned on for initialization (step ①). Next, a blood bag (quadruple bag for removing leukocyte) containing 400 ml collected from a blood donor and already subjected to the first centrifugal separation treatment for, for example, 5 minutes with 3000~4000 G is prepared. Centrifugally separated blood bags 2 are set to the automatic solution separating apparatus 20 as shown in FIG. 1. Among the blood bags 2, a parent bag 2a containing total blood of 400 ml is hung on the hooks 7, 7. Also, the first child bag 2b is placed on the tray 35 of the first secondary container holding portion 23A, that is, the bag 2b is placed on the bag receiving tray 104 of the weight measuring portion 101 of FIG. 3.

Furthermore, the second and third child bags 2c and 2d are hung on the hooks 33a and 33b of the weight measuring portion 102, respectively. Furthermore, a tube 12 of the blood bags 2 is set to the first tube clamper 36, a tube 14 to the second tube clamper 37, and tubes 15a and 15b to the third and fourth tube clampers 38 and 39, respectively.

After the blood bag 2 is set to the automatic solution separating apparatus 20, a program for this blood bag 2, that is, the quadruple bag removing leukocyte is selected and read from the memory portion 40 of the automatic solution separating apparatus 1 (step ②).

Then, as the title of such read program is displayed on the liquid crystal display 45, it is judged whether the kind of the blood bag 2 is coincident with the set program by looking at this display (step ③). If the answer of step ③ is negative, the stop switch 44 is turned on for total cancellation and then goes back to step ② in which a right program is selected and read from the memory portion 40. If the answer of step ③ is affirmative, it goes to step ④ in which the first start switch 42 is turned on and then it goes to step ⑤.

In step ⑤, it is judged whether the separation interface level is in a predetermined position by obtaining the result detected by the interface detecting portion 25, that is, whether the parent bag 2a is set in the predetermined position.

At this time, as it is displayed on the liquid crystal display 45, the judgment is made while looking at this. And if the answer of step ⑤ is negative, it goes back to step ④, in which the stop switch 44 is turned on for total cancellation, and after the position of the parent bag 2a is set to the predetermined position, the first start switch 42 is turned on again. If the answer of step ⑤ is affirmative, then it goes to step ⑥, in which it is judged whether the weight measuring portion 101 shows a predetermined weight, that is whether the predetermined kind of the first child bag 2b is set to a predetermined position. It is also judged whether the weight measuring portion 12 shows a predetermined weight, that is, whether the predetermined kind of second child bag 2c and third child bag 2d are set to a predetermined position.

Since this is displayed on the solution crystal display 45, the judgment is made while looking at this and if the answer of step ⑥ is negative, then it goes back to step ④ in which the stop switch 44 is turned on for total cancellation and after the first child bag 2b is set to a predetermined position, the first start switch 42 is turned on again. If the answer of step ⑥ is affirmative, then it goes to step ⑦, in which the first, second, third, and fourth tube clampers 36, 37, 38 and 39 are all closed. A plug member disposed in the solution take-off tube 11 of the parent bag 2a and which can be separated by breaking is folded to communicate the parent bag 2a and the tube 12 with each other and at the same time, a plug member disposed in the solution take-off tube of the third child bag 2d and which can be separated by breaking is folded to communicate the third child bag 2d and the tube 15b with each other.

Then it goes to step ⑧ and the first start switch 42 is turned on and then it goes to step ⑨ in which the first and third tube clampers 36 and 38 are opened and the second and fourth tube clampers 37 and 39 are closed.

Then it goes to step 10, in which the pressure plate 10 of the container pressurizing portion 22 is pivoted to start pressurizing the parent bag 2a. The blood plasma layer C of the parent bag 2a starts transferring into the second child bag 2c.

Then it goes to step 11, in which it is judged whether the interface between the blood plasma layer C and the mucosa layer D has reached the predetermined set position by the interface detecting portion 25. If the answer of step 11 is negative, then it goes back to step 10 in which the pressurization of the pressure plate 10 is kept going on so as to feed the blood plasma layer C into the second child bag 2c.

If the answer of step 11 is affirmative, then it goes to step 12, in which the first and second tube clampers 36 and 37 are opened and the third and fourth tube clampers 38 and 39 are closed and a portion of the blood plasma layer C and a portion of the mucosa layer D and red blood corpuscle layer E are transferred into the first child bag 2b. Then, it goes to step 13 in which the result measured by the weight measuring portion 101 is obtained and it is judged whether the blood weight entered into the first child bag 2b became 30 g. If the answer of step 13 is negative, then it waits until the weight becomes 30 g without going to the next step. If the answer of step 13 is affirmative, then it goes to step 14, in which pressurization of the pressure plate 10 is stopped and then it goes to step 15.

In step 15, the second and third tube clampers 37 and 38 are opened and the first and fourth tube clampers 36 and 39 are closed. Therefore, the blood plasma layer C entered into the second child bag 2c is transferred into the first child bag 2b by natural flow-down. Then it goes to step 16, in which the result measured by the weight measuring portion 101 is obtained and it is judged whether the weight of the blood plasma entered into the first child bag 2b became 30 g + 40 g = 70 g. If the answer of step 16 is negative, then it waits until the weight becomes 70 g without going to the next step.

If the answer of step 16 is affirmative, then it goes to step 17, in which the first and fourth tube clampers 36 and 39 are opened and the second and third tube clampers 37 and 38 are closed. Therefore, the additive solution of red blood corpuscle within the third child bag 2d is transferred into the parent bag 2a by natural flow-down. Then it goes to step 18, in which the result measured by the weight measuring portion 101 is obtained and it is judged whether the weight of the additive solution of red blood corpuscle entered into the parent bag 2a became 90 g. If the answer of step 18 is negative, then it waits until the weight becomes 90 g without going to the next step.

If the answer of step 18 is affirmative, then it goes to step 19 wherein the stop switch is actuated to become END and the blood component separating operation subjected to the first centrifugal separation work is finished. Thereafter, the tubes 12 and 15a are sealed by a tube sealer, etc. and then the parent bag 2a and the second child bag 2c are cut out from the blood bag 2. Such cut-out parent bag 2a and second child bag 2c are stored in a predetermined place.

Next, function of the above embodiment will be described.

① As the light emitting apparatus 121 constituting the interface detecting portion 25 includes a plurality of light emitting diodes arranged in parallel relation in the upper and lower direction substantially along the interface moving direction of the blood bag 2, changes in transmitting light quantity can be observed at a plurality of positions along the interface moving direction within the blood bag 2 by either absolutely or relatively evaluating among the light emitting elements the light receiving quantity of the light receiving apparatus 122 corresponding to each light emitting diode. Therefore, the apparatus can be simplified and miniaturized without providing a moving mechanism for the light emitting apparatus 121 and the light receiving apparatus 122. In addition, change in setting of the solution interface within the blood bag can be made with ease.

(2) The setting position by the interface setting portion 50 can be adjusted by rewriting the data stored in the memory portion 40, the setting can be changed with ease, and the various components of the solution can be separated with accuracy in accordance with difference in kind of the blood bags 2 and in separating method thereof. At this time, the set interface position stored in the memory portion 40 is not erased even when the main electric power source is cut off due to power failure or the like, and the same set interface position can be maintained repeatedly unless the same is rewritten.

(3) Since the light receiving apparatus 122 is formed of a plate-like light receiving diode, it becomes compact and the apparatus can be miniaturized.

(4) When the sequence unit 26 employs the relative value detecting method which is referred to under the above items (B) and (C), the following effects (a)~(c) can be obtained.

(a) Strong against dirt or stain of the light emitting diode and light receiving diode.

(b) Strong against aging change of the light emitting diode and light receiving diode.

(c) Regarding disturbance light, adverse effect therefrom can be canceled (When the power is active, the disturbance light is corrected, but this can likewise cope with a case where the level of disturbance light is changed because of passage of time such as day to night or night to day while in use).

(5) By using an infrared light emitting diode as the light emitting apparatus 121 constituting the interface detecting portion 25, detecting sensibility can be increased. It is noted, however, that as the infrared light emitting diode is not a visible light, it cannot be recognized by sight even if it is lighted up.

Therefore, by providing a confirmation displaying apparatus 123 comprising a visible light emitting diode in parallel and arranging it to be lighted up simultaneously, the following effects (a)~(c) can be obtained.

(a) By lightening up the set position when a detecting position is set, it becomes easier to understand by sense.

(b) It can be visually confirmed whether the set position is correct.

(c) It can be known whether the operation is being performed normally by lightening the diode of visible light during operation.

(6) By connecting the infrared light emitting diode of the light emitting apparatus 121 and the confirmation display apparatus 123 in series and lightening them up, disorder of these elements can be found. If either of them gets out of order, they are electically not lighted up.

(7) Since a single weight measuring portion 102 is commonly possessed by a plurality of container holding portions 23B and 23C, the apparatus can be simplified and miniaturized when changed amounts in weight of the respective child bags 2c and 2d are measured.

(8) The results of weight measurement of the respective container holding portions 23B and 23C are the results measured by the same weight measuring portion 10 and therefore, irregularities caused by different weight measuring portions are generated.

(9) The sequence unit 26 recognizes the child bags 2c, 2d which are to be changed in weight this time from the unclamped state of the tubes 15a and 15b and is capable of selectively measuring the amount of weight change of the child bag 2c (or 2d) held by the container holding portion 23B (or 23C) which is participated in the current separating work among a plurality of container holding portions 23B and 23C which are under the control of the weight measuring portions 102.

10 The set solution quantity which should be contained in the respective child bags 2b~2d can be adjusted by rewriting the data stored in the memory portion 40, the setting can be changed with ease, and the respective components of the solution can be separated into the respective child bags 2b~2d with high accuracy. At this time, the set quantity stored in the memory portion 40 is not erased even when the main electric power source is cut off due to power failure or the like, and the same set solution quantity can be repeatedly maintained unless it is rewritten.

FIG. 16 is a flowchart showing the operation for a case where a quadruple bag (additive solution is not present) for removing leukocyte already subjected to the first centrifugal separation treatment is used in the solution separating apparatus.

In FIG. 16, the procedures from step (1) to step 16 is exactly the same as for the quadruple bag of FIG. 15 in which the additive solution is present.

And in step 17, the first and third tube clampers 36 and 38 are opened, and the second and fourth tube clampers 37 and 39 are closed, and the blood plasma in the second child bag 2c is transferred into the parent bag 2a. And in step 18, the content in the second child bag 2c is reduced down to 160 g, the weight measuring portion 102 measures this fact, and the first and third tube clampers 36 and 38 are closed. Then it goes to step 19 in which the stop switch 44 is turned on for END, and the separating operation of blood components subjected to the first centrifugal separating treatment is finished. Then, after the tubes 12 and 15a are sealed by a tube sealer, etc., the parent bag 2a and the second child bag 2c are cut out from the blood bag 2. Such cut out parent bag 2a and second child bag 2c are kept in a predetermined place.

EFFECT OF THE INVENTION

According to the present invention as claimed in claims 1 through 8, when the respective components of the solution divided in the container are separated, at the time the solution interface within the container which should be on a final stage of separating operation is set to a predetermined position and the interface detected by the interface detecting portion recognizes the timing the interface detected by the interface detecting portion has reached the set interface position, the apparatus can be simplified and miniaturized. In addition, the setting of the solution interface can be changed with ease.

Also, according to the invention as claimed in claims 9 through 11, at the time the solution separating operation is performed using a plurality of containers connected through tubes and changes in weight of the respective containers are measured, the apparatus can be simplified and miniaturized. In addition, irregularities in result of weight measurement in the respective container holding portions can be prevented.

What is claimed is:

1. A solution separating apparatus comprising:
a container holding portion for holding a flexible container, the container containing a solution divided into layers, the container holding portion including a container pressurizing portion for pressurizing a flexible container held by said container holding portion, and for pushing out a portion of the solution contained in said container for separation;
an interface detecting portion for detecting a position of an interface of the layers of the solution divided in said container;
an interface setting means for setting an interface setting position for said container; and
a control unit for recognizing that an interface detected by said interface detecting portion has reached said interface setting position in accordance with an interface setting position set by said interface setting means and an interface position detected by said interface detecting portion;
said interface detecting portion comprising a light emitting apparatus disposed to one side of the container and a light receiving apparatus disposed to another side of the container with the container held by said container holding portion sandwiched therebetween;
said light emitting apparatus comprising at least three light emitting elements which are repeatedly turned on in order, and which are disposed in parallel in a substantially moving direction of said interface within said container;
said control unit including means for controlling a position for a detecting operation position of said interface detecting portion so that it corresponds to the interface setting position set by said interface setting means for a container received by said container holding portion;
a main one of said at least three light emitting elements located in said detection operation position;
an upper one of said light emitting elements and a lower one of said light emitting elements being located respectively at an upper side and a lower side of said detection operation position and being repeatedly operated to emit light in sequence;
said light receiving apparatus receiving quantities of light at the light emitting timing of said light emitting elements, the received light quantities comprising a main light receiving quantity, an upper light receiving quantity and a lower light receiving quantity; and
said control unit further including means for recognizing that the interface in said container has reached the interface setting position under the conditions that a difference between the main light receiving quantity and the lower light receiving quantity exceeds a reference level.

2. The solution separating apparatus of claim 1, wherein said control unit further includes a non-volatile memory means for storing the position set by said interface setting means, said memory means being capable of rewriting and reading said stored data, said stored data being retained in said non-volatile memory means even when a power source is cut off.

3. The solution separating apparatus of claim 2, wherein said light receiving apparatus comprises a plate-like light receiving element.

4. The solution separating apparatus of claim 1, wherein said light receiving apparatus comprises a plate-like light receiving element.

5. The solution separating apparatus of claim 1, wherein said control unit includes means for recognizing that said light receiving quantity substantially equals one-half of a difference between said upper and lower light receiving quantities.

6. The solution separating apparatus of claim 1, wherein said light emitting elements comprise infrared light emitting elements, and wherein a visible light emitting element is juxtaposed to each of said light emitting elements.

7. The solution separating apparatus of claim 6, wherein said infrared light emitting elements are connected in series to corresponding visible light emitting elements.

8. A solution separating apparatus comprising:
a plurality of container holding portions for holding a plurality of flexible containers connected with each other by tubes, said flexible containers containing a solution divided into layers;
a plurality of tube clampers for clamping the tubes communicating with said respective containers;
a container pressurizing portion for pressurizing a flexible container containing said solution divided into layers, and including means for pressurizing a flexible container held by said container holding portion, and for pushing out a portion of the solution contained in said container for separation;
an interface detecting portion for detecting a position of an interface of the layers of the solution divided in said container;
an interface setting means for setting an interface setting position for said container; and
a control unit for controlling said tube clampers and said container pressurizing portion for transferring a solution between said container pressurized by said container pressurizing portion and containers communicated with each other through unclamped tubes, and for clamping said tubes through said tube clampers when an interface detected by said interface detecting portion has reached the interface setting position in accordance an interface setting position set by said interface setting means and an interface position detected by said interface detecting portion;
said interface detecting portion comprising a light emitting apparatus disposed to one side of the container and a light receiving apparatus disposed to another side of the container with the container held by said container holding portion sandwiched therebetween;
said light emitting apparatus comprising at least three light emitting elements which are repeatedly turned on in order, and which are disposed in parallel in a substantially moving direction of said interface within said container;
said control unit including means for controlling a position for a detecting operation position of said interface detecting portion so that it corresponds to the interface setting position set by said interface setting means for a container received by said container holding portion;

a main one of said at least three light emitting elements located in said detection operation position;

an upper one of said light emitting elements and a lower one of said light emitting elements being located respectively at an upper side and a lower side of said detection operation position and being repeatedly operated to emit light in sequence;

said light receiving apparatus receiving quantities of light at the light emitting timing of said light emitting elements, the received light quantities comprising a main light receiving quantity, an upper light receiving quantity and a lower light receiving quantity; and said control unit further including means for recognizing that the interface in said container has reached the interface setting position under the conditions that a difference between the main light receiving quantity and the lower light receiving quantity exceeds a reference level.

9. The solution separating apparatus of claim 8, wherein said control unit further includes non-volatile memory means for storing the position set by said interface setting means, said memory means being capable of rewriting and reading said stored data, said stored data being retained in said non-volatile memory means even when a power source is cut off.

10. The solution separating apparatus of claim 9, wherein said light receiving apparatus comprises a plate-like light receiving element.

11. The solution separating apparatus of claim 8, wherein said light receiving apparatus comprises a plate-like light receiving element.

12. The solution separating apparatus of claim 8, wherein said control unit includes means for recognizing that said light receiving quantity substantially equals one-half of a difference between said upper and lower light receiving quantities.

13. The solution separating apparatus of claim 8, wherein said light emitting elements comprise infrared light emitting elements, and wherein a visible light emitting element is juxtaposed to each of said light emitting elements.

14. The solution separating apparatus of claim 13, wherein said infrared light emitting elements are connected in series to corresponding visible light emitting elements.

* * * * *

UNITED STATES PATENT AND TRADEMARK OFFICE
CERTIFICATE OF CORRECTION

PATENT NO. : 5,124,030

DATED : June 23, 1992

INVENTOR(S) : TANOKURA et al

It is certified that error appears in the above-identified patent and that said Letters Patent is hereby corrected as shown below:

Column 4, line 1, after "invention", insert -- , --.

Column 4, lines 30-31, after "invention", insert -- , --.

Column 4, line 54, delete "is that".

Column 5, line 63, after "feature of", insert --the invention,--.

Signed and Sealed this

Eighteenth Day of January, 1994

Attest:

BRUCE LEHMAN

Attesting Officer          Commissioner of Patents and Trademarks

UNITED STATES PATENT AND TRADEMARK OFFICE
CERTIFICATE OF CORRECTION

PATENT NO. : 5,124,030
DATED : June 23, 1992
INVENTOR(S) : Tanokura et al

It is certified that error appears in the above-indentified patent and that said Letters Patent is hereby corrected as shown below:

Column 11, line 45, Formula (2):

Change "$...Y_{n-2})/2$" to --$...Y_{n+2})/2$--.

Signed and Sealed this

Twenty-second Day of February, 1994

Attest:

BRUCE LEHMAN

Attesting Officer

Commissioner of Patents and Trademarks